US012675874B2

(12) United States Patent
Moriconi et al.

(10) Patent No.: US 12,675,874 B2
(45) Date of Patent: Jul. 7, 2026

(54) GRAPH-BASED HEMODYNAMICS FOR BIOMARKERS OF NEUROVASCULAR RESILIENCE

(71) Applicants:King's College London, London (GB); UCL Business Ltd, London (GB)

(72) Inventors: Stefano Moriconi, London (GB); Manuel Jorge Machado Cardoso, London (GB); Parashkev Nachev, London (GB); Sebastien Ourselin, London (GB)

(73) Assignees: King's College London, London (GB); UCL Business Ltd, London (GB)

( * ) Notice: Subject to any disclaimer, the term of this patent is extended or adjusted under 35 U.S.C. 154(b) by 303 days.

(21) Appl. No.: 17/754,302

(22) PCT Filed: Sep. 30, 2020

(86) PCT No.: PCT/GB2020/052368
§ 371 (c)(1),
(2) Date: Mar. 29, 2022

(87) PCT Pub. No.: WO2021/064372
PCT Pub. Date: Apr. 8, 2021

(65) Prior Publication Data
US 2023/0079772 A1     Mar. 16, 2023

(30) Foreign Application Priority Data
Sep. 30, 2019    (GB) ...................................... 1914089

(51) Int. Cl.
*G06T 7/00*       (2017.01)
*G06T 7/12*       (2017.01)
(Continued)

(52) U.S. Cl.
CPC .............. *G06T 7/0012* (2013.01); *G06T 7/12* (2017.01); *G06T 7/174* (2017.01); *G16H 50/50* (2018.01); *G06T 2207/30101* (2013.01)

(58) Field of Classification Search
CPC ......... G06T 7/0012; G06T 7/12; G06T 7/174; G06T 2207/30101; G16H 50/50
See application file for complete search history.

(56) References Cited

U.S. PATENT DOCUMENTS

| 6,201,543 B1 | 3/2001 | O'Donnell |
| 12,536,687 B2 | 1/2026 | Moriconi et al. |

(Continued)

FOREIGN PATENT DOCUMENTS

| EP | 3 477 592 A1 | 5/2019 |
| KR | 20160053325 A | 5/2016 |

(Continued)

OTHER PUBLICATIONS

Leventon et al., "Statistical Shape Influence in Geodesic Active Contours", 5th IEEE Embs International Summer School on Biomedical Imaging, 2002 (Year: 2002).*

(Continued)

*Primary Examiner* — Qian Yang
(74) *Attorney, Agent, or Firm* — Hamilton, Brook, Smith & Reynolds, P.C.

(57) ABSTRACT

Examples of the present disclosure relate to an apparatus comprising input circuitry configured to acquire imaging data corresponding to a branched biological structure. The apparatus further comprises image processing circuitry configured to: extract, from the imaging data, a configuration of the branched biological structure; determine graph data indicative of the configuration of the branched biological structure; and detect, based on the graph data, a biological characteristic of the branched biological structure.

13 Claims, 7 Drawing Sheets

(51) Int. Cl.
G06T 7/174 (2017.01)
G16H 50/50 (2018.01)

(56) References Cited

U.S. PATENT DOCUMENTS

| | | | |
|---|---|---|---|
| 2008/0085042 A1 | 4/2008 | Trofimov et al. | |
| 2011/0093243 A1 | 4/2011 | Tawhai et al. | |
| 2014/0379318 A1 | 12/2014 | Spilker | |
| 2015/0164452 A1 | 6/2015 | Choi et al. | |
| 2015/0164453 A1* | 6/2015 | Choi | A61B 6/503 |
| | | | 600/407 |
| 2016/0008085 A1 | 1/2016 | Itai | |
| 2016/0300350 A1 | 10/2016 | Choi | |
| 2017/0178226 A1 | 6/2017 | Graham et al. | |
| 2017/0270705 A1* | 9/2017 | Hopfgartner | A61B 6/5211 |
| 2019/0023060 A1* | 1/2019 | Maertens | B44F 9/04 |
| 2023/0106527 A1 | 4/2023 | Moriconi et al. | |

FOREIGN PATENT DOCUMENTS

| | | | |
|---|---|---|---|
| WO | 2009/050304 A1 | 4/2009 | |
| WO | 200906475 A1 | 5/2009 | |
| WO | 2009064715 A1 | 5/2009 | |
| WO | 20170178226 A1 | 10/2017 | |
| WO | 2021064372 A1 | 4/2021 | |
| WO | 2021/161038 A1 | 8/2021 | |

OTHER PUBLICATIONS

Cebral et al., "From medical images to anatomically accurate finite element grids", Int. J. Numer. Meth. Engng 2001; 51:985-1008 (Year: 2001).*

International Preliminary Report on Patentability and Written Opinion for PCT/GB2020/052368, titled: Apparatus and Method for Determining a Biological Characteristic Date Mailed: Apr. 5, 2022.

International Search Report and Written Opinion for PCT/GB2020/052368, titled: Apparatus and Method for Determining a Biological Characteristic Date Mailed: Jan. 13, 2021.

Kiousis, D., E., et al.: "A Numerical Model to Study the Interaction of Vascular Stents with Human Atherosclerotic Lesions", Annals of Biomedical Engineering, Kluwer Academic Publishers-Plenum Publishers, Ne, vol. 35, No. 11, (2007).

L. Antiga, et al. AneuriskWeb, The Aneurisk Dataset Repository. URL:http://ecm2.mathcs.emory.edu/aneuriskweb/, 2011.

L. Antiga and D. Steinman. The Vascular Modeling Toolkit. URL:http://www.vmtk.org, 2008.

E. Bullitt, "Healthy MR Database: Designed Database of MR Brain Images of Healthy Volunteers," ITK-TubeTK, 2007.

J. R. Cebral, et al., "Characterization of cerebral aneurysms for assessing risk of rupture by using patient-specific computational hemodynamics models," Am J Neuroradiol, 2005.

C. Chnafa, et al., "Improved reduced-order modelling of cerebrovascular flow distribution by accounting for arterial bifurcation pressure drops," J Biomech, 2017.

F. E. Fossan, et al., "Optimization of opological complexity for one-dimensional arterial blood flow models," J Royal Soc Interface, 2018.

A. Kanitsar, et al., "Curved planar reformation," In Proc Conf Visual IEEE, 2002.

E. Konukoglu, et al., "A Recursive Anisotropic Fast Marching Approach to Reaction Diffusion Equation: Application to Tumor Growth Modeling," In IPMI, 2007.

R. Kwitt, et al., "Studying Cerebral Vasculature Using Structure Proximity and Graph Kernels," In MICCAI, 2013.

Leventon et al., "Statistical Shape Influence in Geodesic Active Contours," 5th IEEE EMBS International Summer School on Biomedical Imaging, 2002.

C. Mathers, et al., "The Global Burden of Disease," WHO, 2008.

S. Moriconi, et al., "Inference of cerebrovascular topology with geodesic minimum spanning trees," IEEE TMI, vol. 38, No. 1, Jan. 2019.

O. Onaizah, et al., "A model of blood supply to the brain via the carotid arteries: Effects of obstructive vs. sclerotic changes," Med Eng Phys, 2017.

J. Ryu, et al., "A coupled lumped-parameter and distributed network model for cerebral pulse-wave hemodynamics," J Biomech Eng, 2015.

M. Shojima, et al., "Magnitude and role of wall shear stress on cerebral aneurysm: computational fluid dynamic study of 20 MCA aneurysms," Stroke, 2004.

J. A. Sethian, "A Fast Marching Level Set Method for Monotonically Advancing Fronts," PNAS, 1996.

D. Steinman, et al., "Computational modeling of arterial biomechanics: Insights into pathogenesis and treatment of vascular disease," J Vasc Surg, 2003.

C. Taylor and J. Humphrey, "Open problems in computational vascular biomechanics: Hemodynamics and arterial wall mechanics," CMAME, 2009.

B. Urick, et al., "Review of patient-specific vascular modeling: template-based iso-geometric framework and the case for CAD," Arch Comput Methods Eng, 2019; 26:381-404. Published on line Nov. 28, 2017.

M. D. Vitturi, "Navier-Stokes equations in cylindrical coordinates," 2016.

"TubeTK, Segmentation, Registration, and Analysis of Images with Tubular Structures," Downloaded from https://web.archive.org/web/20120705040439/http://www.tubetk.org/ on Aug. 12, 2025, Kitware.

* cited by examiner

100

105    110

IMAGING
DATA
→ INPUT
CIRCUITRY

IMAGE PROCESSING
CIRCUITRY

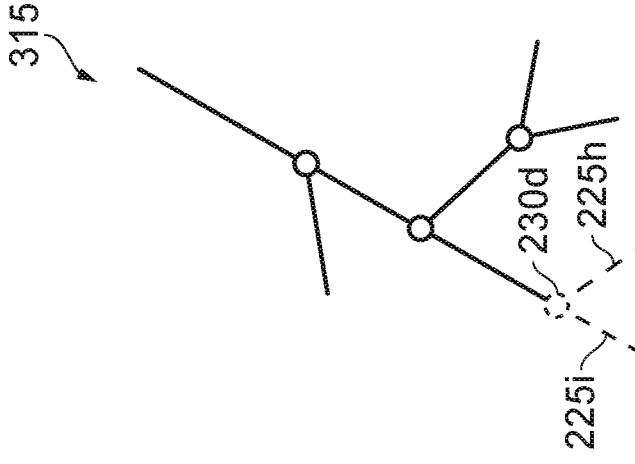
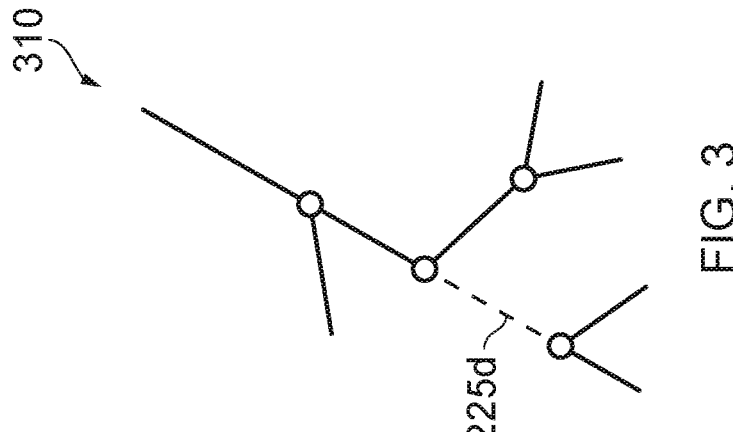
FIG. 3
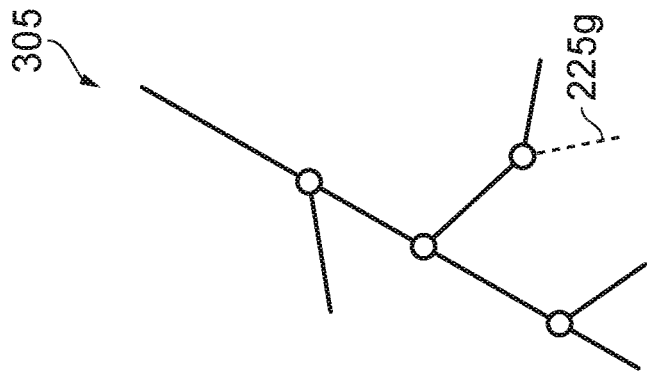

FIG. 4A                    FIG. 4B $\rho = 20.8$ $\rho = 23.7$

GRAPH-BASED HEMODYNAMICS FOR BIOMARKERS OF NEUROVASCULAR RESILIENCE

This application is the U.S. National Stage of International Application No. PCT/GB2020/052368, filed on Sep. 30, 2020, which designates the U.S., published in English, and claims priority under 35 U.S.C. § 119 or 365 (c) to Great Britain Application No. 1914089.6, filed on Sep. 30, 2019. The entire teachings of the above applications are incorporated herein by reference.

The presented technique relates to the field of image processing. More particularly, it relates to determining characteristics of branched biological structures based on imaging data.

Branched biological structures, such as networks of blood vessels, networks of pulmonary vessels, and so on, can be extremely complex. This complex structure can be imaged using techniques such as angiography. However, the complexity can lead to difficulty in processing such images to detect characteristics of the imaged structures, for example relating to fluid flow within the structure: even where the layout of such a structure can be determined, significant computing resources can be required to analyse the structure and determine biological characteristics thereof. As well as increasing cost, this typically results in it being unfeasible to analyse a complex structure in real time. Whilst the complexity can be reduced by analysing only a relatively small portion of a complex structure, such as for example the layout of blood vessels in a specific part of a brain as opposed to an entire neurovascular network, this limits the extent to which biological characteristics can be accurately detected. For example, it may be difficult or impossible to accurately determine characteristics of one part of the biological structure without taking into account how that part interacts with the rest of the structure.

There is thus a desire for improved apparatus and methods for analysing imaging data, corresponding to branched biological structures, to detect biological characteristics of such structures.

In one example configuration, there is provided an apparatus comprising:

input circuitry configured to acquire imaging data corresponding to a branched biological structure; and image processing circuitry configured to:

extract, from the imaging data, a configuration of the branched biological structure;

determine graph data indicative of the configuration of the branched biological structure; and detect, based on the graph data, a biological characteristic of the branched biological structure.

In a further example configuration, there is provided a method comprising:

acquiring imaging data corresponding to a branched biological structure;

extracting, from the imaging data, a configuration of the branched biological structure;

determining graph data indicative of the configuration of the biological structure;

detecting, based on the graph data, a biological characteristic of the branched biological structure.

In a further example configuration, there is provided a computer-readable medium comprising computer-implementable instructions for causing a computer to become configured as the aforementioned apparatus, or to become configured to carry out the aforementioned method.

The present technique will be described further, by way of illustration only, with reference to examples thereof as illustrated in the accompanying drawings, in which:

FIG. 1 shows schematically an apparatus 100 according to examples of the present disclosure;

FIGS. 2A to 2C schematically illustrate an example of determination of graph data indicative of a configuration of a branched biological structure;

FIG. 3 schematically illustrates how a statistical likelihood associated with a biological characteristic can be determined by iteratively modifying the above-described graph data;

FIGS. 4A to 4E illustrate an example of determination of graph data from image data, followed by the modification of that data;

Figure 1:
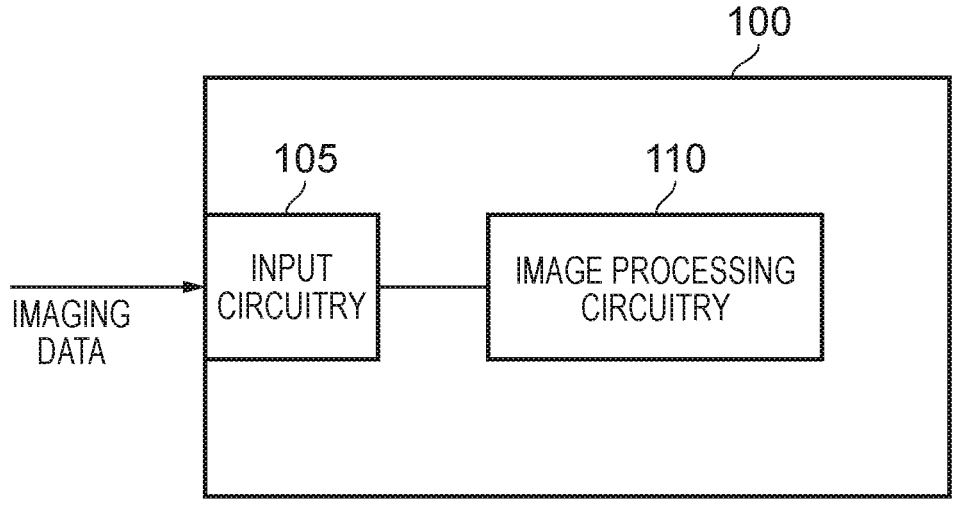

As stated above, an apparatus according to an aspect of the present disclosure comprises input circuitry configured to acquire imaging data corresponding to a branched biological structure. The branched biological structure comprising a tubular biological structure comprising a fluid, such as a network of blood vessels for example within an organ such as a brain, kidney or eye. As another example, the branched biological structure may be a pulmonary structure such as a network of air passages in a lung. The imaging data may be a two-dimensional image acquired by angiography, for example of the blood vessel structure of a human or animal organ. As another example, the imaging data may be an image acquired by computed tomography imaging of the vessels of a human or animal lung. In other examples, the imaging data may be a three-dimensional representation, or another form of representation.

The apparatus comprises image processing circuitry. The image processing circuitry may be dedicated circuitry or general-purpose circuitry. For example, the image processing circuitry may be a computer processor such as a central processing unit (CPU) or graphical processing unit (GPU) executing computer instructions defining the following image processing steps. As another example, the image processing circuitry may be implemented in one or more application-specific integrated circuits (ASICs) or field-programmable gate arrays (FPGAs).

The image processing circuitry is configured to extract, from the imaging data, a configuration of the branched biological structure. This may comprise isolating the branched structure from the rest of an image and then determining the layout of branches of the structure, for example including lengths and widths of each branch as well as how each branch is connected to other branches.

The image processing circuitry is configured to determine graph data indicative of the configuration of the branched biological structure. For example, the graph data may comprise edges corresponding to branches of the branched biological structure and vertices corresponding to connections between said branches of the branched biological structure. The graph data provides an efficient way to represent the configuration of the branched biological structure. The image processing circuitry may be configured to, as part of the determining of the graph data, determine for each edge at least one geometrical property of the corresponding branch of the branched biological structure. Such geometrical properties may include (but are not limited to) a length, width, curvature and/or elasticity of the corresponding branch. The graph data can thus efficiently represent the geometry of the branched structure, without incurring the storage and processing overhead that would be associated with a more complex representation such as a three-dimensional surface model of the structure.

The image processing circuitry is configured to detect, based on the graph data, a biological characteristic of the branched biological structure. The biological characteristic may for example be an indication of a resilience or susceptibility of the biological structure to damage. For example, where the biological structure is a vascular network of a human brain, the biological characteristic may be a resilience of the brain to a surgical modification thereof, or a susceptibility of the brain to an event such as a stroke. The image processing circuitry can thereby make use of the efficient representation of the biological structure to efficiently determine the biological characteristic, using significantly less processing resources than would be used in comparative systems in which a less efficient representation of the biological structure is used. This allows the present apparatus to determine biological characteristics of significantly more complex biological structures than would be possible with some comparative systems that do not implement the present disclosure. For example, implementations of the present disclosure could analyse a complex structure such as a substantially complete neurovascular network, whereas comparative systems in which a less efficient representation of the biological structure is used may be limited to (within a reasonable time) analysing smaller, i.e. incomplete, portions of such a biological structure. The present disclosure thus provides more accuracy in determination (i.e. by providing more accurate approximation) of biological characteristics. For example, the resilience of a biological structure to a surgical modification may depend on the layout of that structure in locations far from the modification, which may not be captured in an analysis of a mere portion of the structure.

The computational efficiency of examples of the present disclosure also allows such examples to be implemented in real-time, for example to inform decisions as to particular surgical modifications that are to be made. For example, the impact on a neurovascular network of a potential physical modification of the network, such as by way of a surgical intervention, can be assessed prior to performing that modification even where the modification is to be performed as a matter of urgency. As an example, a person who is to receive emergency surgery for a stroke can be assessed to determine the impact of that surgery, or to inform a decision as to which of various surgical options would have the least impact on brain function.

The image processing circuitry may be configured to determine, for each vertex of the graph data and based on the aforementioned geometric properties associated with each edge, at least one fluid property of the corresponding connection of the branched biological structure. The image processing circuitry may determine these fluid properties by performing computational fluid dynamical modelling with the graph data as an input. Examples of such fluid properties include fluid pressure at the corresponding connection and fluid flow through the corresponding connection. These fluid properties can then be used in the detection of the biological characteristic. For example, the impact of a blockage in a given branch of the biological structure may depend on the pressure and flow at nearby vertices: the present apparatus can thus use these fluid properties to determine the susceptibility of an individual to such a blockage. This technique can be extended to determine the functional resilience of the individual to such a blockage in a number of scenarios.

In an example, the image processing circuitry is configured to modify the graph data and re-detect, based on the modified graph data, the biological characteristic of the branched biological structure. The modification may comprise at least one of removing at least one edge of the graph data, removing at least one node of the graph data, and modifying a physical property such as a width associated with at least one edge of the graph data. This modification may for example correspond to a modification of the configuration of the biological structure. For example, removal of an edge or node may correspond to a blockage or removal of a branch or connection of the biological structure. Similarly, modification of a width associated with an edge may correspond to a partial occlusion of the biological structure. As a further example, insertion of a new edge or node may correspond to a surgical addition of a new connection or branch, for example by way of a bypass implant or re-canalisation. The apparatus can thus determine the impact on the biological structure of such modifications. The modification may be a biologically plausible modification. The apparatus can thus avoid wasting processing resources analysing modifications that would not plausibly occur such as, for example, flow rates or pressures that would not be expected to occur in the biological structure in question. The modification may be determined based on a potential future physical modification of the biological structure, such as a planned or potential surgical intervention or a defect such as a pathology which may occur. The presently described apparatus can thus be used to determine the impact on a person of such a surgical intervention and/or of a pathology to which the person is potentially susceptible.

In an example, the image processing circuitry is configured to iteratively repeat the modifying of the graph data and the re-detecting of the biological characteristic. The image processing circuitry is then further configured to, based on the detection of the biological characteristic and the re-detections of the biological characteristic, determine a statistical likelihood associated with the biological characteristic. In this manner, the apparatus can for example determine a statistical susceptibility of the biological structure to a pathology. For example, a vascular network could be iteratively analysed to determine the likelihood that partial occlusions in various locations within the network could lead to a breakdown in the proper functioning of the network (such as its ability to effectively deliver blood). If this likelihood is relatively high, it can be determined that the network is particularly susceptible to arterial plaque and other sources of arterial occlusion. Conversely, if this likelihood is relatively low, it can be determined that the network is particularly resistant to arterial occlusion. Such iterative analysis is enabled by the efficient representation of the biological structure by way of graph data, and would be very computationally intensive in comparative systems in which such an efficient representation is not used.

The graph data may be a hierarchical graph such as a strict tree graph. Alternatively, the graph data may be more general graph data which, for example, permits non-hierarchical features such as loops, or other arbitrarily branching structures. Such graph data, which does not enforce a priori assumptions regarding a hierarchical and/or pre-defined parent-child relationships, increases the range of biological structures, and pathologies thereof, which can be represented. For example, this allows modelling of healthy anastomoses of the vasculature in the brain such as the complete circle of Willis (arterial-side), and the intra-cavernous sinuses, the basilar plexus and the marginal sinus (venous-side), where the connected configuration of the branches determine cycles or closed loops. This also allows modelling of diseased cases of multiple nested anastomoses from arterio-venous malformations and neoplastic vascularisation (angiogenic growth), resulting in a tangle of interconnected loops. As a further example, this allows modelling of whole body anastomoses at different scales, i.e. pulmonary and peripheral circulation (large scale), and the capillary bed joining artery and veins (small scale) in a closed loop.

Conversely, in comparative examples in which a hierarchical structure is explicitly or implicitly enforced, only specific (e.g. airways), limited and localised portions of the branching biological anatomy (vascular) can be correctly modelled. Other more complex, cyclic, anatomical structures cannot be represented. Comparative examples which utilise acyclic tree approximations may require arbitrary graph pruning and simplification, which can be partial and incomplete with respect of the underlying biological network. Furthermore, modelling branching structures only with acyclic trees can bias the estimation and the subsequent analysis of the simulation, which has the form of a strictly feed-forward relationship. The present disclosure thus provides a significant improvement of model accuracy when compared with such comparative examples.

The use of non-hierarchical graph data also allows the characterisation of complex fluid-dynamic parameters of the branching structure in line with the actual underlying anatomy, such as multiple sources of territorial supply and their associated bio-mechanical parameters, as well as mutual interactions of fluid-dynamic components within a (sub-) network, i.e. the dynamic compensation and the intrinsic autoregulation mechanisms.

This is particularly advantageous in modelling fluid-dynamic behaviours of complex networks, e.g.:

a healthy neurovascular arterial sub-network, which consists of four main vascular roots (sources), namely, the left and right carotid arteries (anterior), and the left and right vertebral arteries (posterior), which connect and the main anastomosis of the circle of Willis (cyclic vascular structure) and further branch with possible localised collateral vessels. Each root contributes to the blood supply in the brain. However, each territorial flow depends on each bio-mechanic characteristic of each root (source), and, at the same time, on the balanced and compensatory interaction of the bio-mechanic characteristics of all the connected vessels constituting the surrounding (sub-) network (branches and leaves). The root-specific downstream (or upstream) flow and effects cannot be independently determined, since a multiplicity of connected structures simultaneously contribute. Nor can the ratio and distributions of the respective contributions to the brain territorial blood supply be trivially determined in a dynamic setup, as this includes latencies and mechanical energy loss induced by the physical pathways morphology and by the subject-specific anatomical configuration of the connected branching pattern.

in case of disease, such as stenosis (narrowing), aneurysm (dilation), calcification (stiffening), and ischaemia (occlusion), etc., the fluid-dynamic behaviour strongly depends on the intrinsic mechanic compensation of the connected vascular configuration of the whole network. Such network compensation mechanisms are complex. Downstream effects of a series or combination of the above pathological conditions at different locations in the (sub-) network cannot be predicted by disregarding the simultaneous interaction (feed-forward and feedback) of mutual effects in a connected structure with anatomical redundancy.

similar autoregulation and compensation mechanisms happening on different scales on the circulation of the whole body, not only on the neurovascular one, for example in the kidneys and the heart. Collateral flows, local vortices, eddy developments within the tortuous vascular network, and occasional backflow (regurgitation) can happen in both healthy and diseased cases at different scales of the anatomical compartment and can ultimately affect the autoregulation and determine the occurrence of pathology.

In the comparative example of a hierarchical tree, a single root (inlet) is determined, and the subsequent flow deterministically subdivides through the branches (links) down to the terminal leaves (outlets). In such a comparative example, the simulation profile has the form of a one-way feed-forward laminar flow, and downstream effects cannot account for multiple sources (inlets) and multiple interactions of a complex network. Analogously, the mutual compensation mechanisms within a tree are inexistent by definition. Therefore, possible (up- or) downstream effects of a neighbouring connected network to the tree cannot be correctly modelled in a dynamic setup.

The use of non-hierarchical graph data also the modelling, and simulation of alterations, of the connected nature of the branching biological structure to account for different biological phenotypes of branching pattern, and to account for a number of associated physio-pathological scenarios.

This is particularly advantageous in the evaluation, analysis and prediction of:

risk of adverse events and localisation of focal pathological points (e.g. in stroke or in critical territorial supply failure) upon the subject-specific vascular phenotype. Since multiple phenotypes of connected configurations can be modelled with graphs, simulations can identify a family of subjects that are more prone to develop life-threatening pathology.

the resilience of a redundant network: diffusion and territorial supply in collaterally connected structures can be evaluated directly via efficient and computationally fast simulations on graphs to support prompt therapeutic inference (e.g. interventional decision-making in case of partial occlusions or other pathology-whether to intervene or not), otherwise characterise the extent of the redundancy (e.g. neoplastic vascularisation) to target specific treatments.

key anatomical structures and pathways of interventional relevance: detection of critical hot-spots and related surgical feasibility in a compact and intuitive way (i.e. problematic junction or branch), given the collateral connectivity, to identify the most suitable treatment (e.g. thrombolysis vs thrombectomy in case of ischaemic stroke) and potentially the most effective surgical planning.

Conversely, with a hierarchical tree alterations of the acyclic configuration are limited and the associated downstream effects are straightforward. Trees can only represent acyclic (sub-) networks, therefore their phenotypical modelling capability is intrinsically limited to a specific case of applications. In real-life scenarios, trees can only adequately model local portions of more complex anatomical networks.

Downstream effects of introduced and simulated alterations are independent and propagate in a feed-forward manner—they do not depend on collateral pathways—e.g. the (complete) stenosis of a 'parent' branch would result in the (complete) reduction of flow in the 'child' sub-tree. Since a tree structure cannot model existing collateral anatomical pathways, it has limited application on optimised and adaptive surgical planning. The route connecting the root to any other branch is unique. The use of non-hierarchical graph data thus provides significant advantages in such a case.

Examples of the present disclosure will now be described with reference to the Figures.

FIG. 1 shows schematically an apparatus 100 according to examples of the present disclosure.

The apparatus 100 comprises input circuitry 105. The input circuitry 105 is configured to acquire imaging data corresponding to a branched biological structure. This image data may for example be acquired from an image capture device, such as a medical imaging apparatus, or from a storage.

The apparatus 100 further comprises image processing circuitry 110. The image processing circuitry may comprise dedicated circuitry or, in other examples, may be implemented within general-purpose circuitry such as processing circuitry. Examples of general-purpose processing circuitry include a central processing unit and a graphical processing unit.

The image processing circuitry 110 is configured to extract, from the imaging data, a configuration of the branched biological structure. The image processing circuitry is configured to then determine graph data indicative of the configuration of the branched biological structure. Examples of how this determination can be performed are described in more detail below.

The image processing circuitry 110 is configured to detect, based on the graph data, a biological characteristic of the branched biological structure. Examples of detection of particular example characteristics are described in more detail below.

Figures 2A, 2B, 2C:
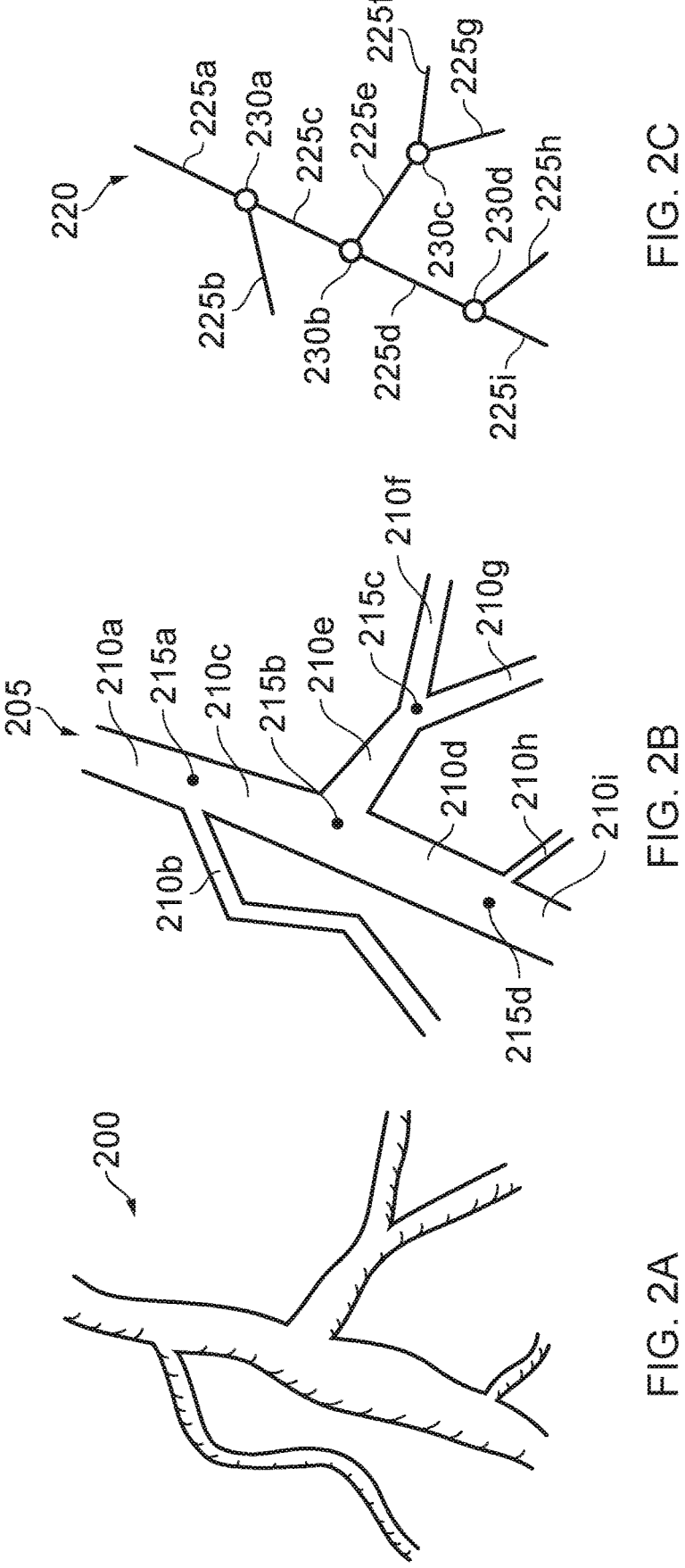

FIGS. 2A to 2C schematically illustrate an example of determination of graph data indicative of a configuration of a branched biological structure.

FIG. 2A schematically illustrates a branched biological structure 200. The branched biological structure 200 is shown as a relatively simple structure for ease of illustration, but in some implementations could be a complex structure such as a large vascular network (for example a substantially complete neurovascular network).

FIG. 2B schematically illustrates the configuration 205 of the branched biological structure 200 as determined by the image processing circuitry 110 of FIG. 1. The configuration has been determined as a series of branches 210a-210i, connected via a series of connections 215a-215d. For example, branches 210a, 210b and 210c are connected via connection 215a. The determined configuration may also include further properties of the branches and/or connections in addition to their topological layout. For example, properties such as lengths, widths and curvatures may be determined for some or all of the branches 210a-210i. Such properties may be determined from imaging data and/or physical examination (such as via biopsy).

FIG. 2C schematically illustrates a connected graph 220 that can be determined based on the configuration 205 of the branched structure. The graph 220 comprises edges 225a-225i, each of which corresponds to a corresponding one of the branches 210a-210h of the configuration 205. The edges 210a-210h of the graph 220 are connected via vertices 230a-230d, each of which corresponds to a corresponding one of the connections 215a-215d of the configuration 205. Further properties of the branches and/or connections, such as those mentioned above, may be stored associated with some or all of the edges 210a-210h and/or vertices 230a-230d. In order to determine the graph 220, the properties of the configuration 205 may be condensed into simplified "lumped parameters".

The graph 220 thus provides an efficient means of representing the branched biological structure 200: the topology of the structure is captured, along with potentially other properties such as length and width of branches, without incurring the computational overhead that would be associated with a more detailed representation such as a full parametrisation of the surface of the branched structure 200. Despite this efficiency of representation, sufficient information regarding the configuration of the structure 200 is captured in the graph 220 to enable biological characteristics of the branched structure to be determined. This determination can thus be performed in an efficient manner.

FIG. 3 schematically illustrates how a statistical likelihood associated with a biological characteristic can be determined by iteratively modifying the above-described graph data.

The above-described graph data 220 can be modified, and the biological characteristic re-determined for each modification. The modifications may be limited to biologically plausible modifications, so that processing power is not wasted on modifications that would not plausibly occur. Also, avoiding biologically implausible modifications reduces the risk of drawing incorrect conclusions regarding the biological characteristic.

FIG. 3 shows three potential modifications 305, 310, 315 of the above-described graph data 220.

In modification 305, edge 225g has been removed (and is consequently shown with a dashed line). This may for example correspond to a blockage in branch 210h of the branched structure, or a surgical removal of branch 210h.

In modification 310, edge 225d has been removed (and is consequently shown with a dashed line). This may for example correspond to a blockage in branch 210d of the branched structure, or a surgical removal of branch 210d.

In modification 315, vertex 230d has been removed. Consequently, edges 225h and 225i (which were connected to vertex 230d) have also been removed. Removed vertex 230d and edges 225h, 225i are shown in dotted lines. This removal may for example correspond to a blockage in connection 215d of the branched structure, which causes branches 210h and 210i to become cut off from the rest of the network. Similarly, this may correspond to a surgical removal of connection 215d and/or branches 210h and 210i.

In general, although not shown in FIG. 3, graphs according to examples of the present disclosure may have loops and thus may not have a tree-like acyclic structure. Such loops can cause a given graph modification to have different downstream impacts, according to the network redundancy.

Such modifications (and potentially other modifications) can be iteratively determined in an efficient manner. If, for example, the branched structure is a neurovascular network and the biological characteristic that is determined relates to blood delivery within the brain, the impact of each modification on blood delivery can be determined. It may for example be determined that modification 305 has a minimal impact, modification 310 has a significant impact, and modification 315 has a moderate impact. Based on this, a statistical likelihood associated with the biological characteristic can be determined. For example, if each modification 305, 310, 315 is deemed to have an equal likelihood of occurring, it may be determined that there is a moderate likelihood of a blockage in the brain causing an impact. This statistical likelihood can be used to draw medical conclusions such as, for example the susceptibility of a patient to such blockages. Conversely, it may be determined that a different patient has a lower likelihood of susceptibility to such blockages. For example, such a lower likelihood of susceptibility may be a consequence of that patient having higher redundancy in the network in question. This higher redundancy may be caused, at least in part, by the presence of anastomoses (which would be represented as loops in the graph). Anastomoses can be part of individual physio-pathological variability and can occur at different locations and scales in networks such as the cardiovascular and neurovascular networks.

Analysis such as this can also be used to model the progression of a pathology, as well as the impact of surgical intervention, in order to draw inform medical decision-making. In general, this allows quantification of the overall vulnerability of a patient to complications such as atherosclerosis, stenosis and tortuosity; life-threatening conditions such as aneurysm rupture and stroke; surgical interventions such as stenting, coiling and recanalization; and long-term follow-up such as ageing, familial and environmental factors.

A more detailed example of the determination of graph data from image data, followed by the modification of that graph data, will now be illustrated with reference to FIGS. 4A-4E.

FIG. 4A shows an angiographic image of the Circle of Willis, a neurovascular structure. This image may for example have been captured using three-dimensional angiographic imaging techniques.

FIG. 4B illustrates an extracted configuration of the Circle of Willis of FIG. 4A. In this example, the extracted configuration is determined by delineating and segmenting the captured image by way of geodesic active contours (G-snakes). The configuration, including layout as well as geometric properties such as width and length of each branch, are thus captured by modelling the Circle of Willis as a series of tubes.

Figure 4C:
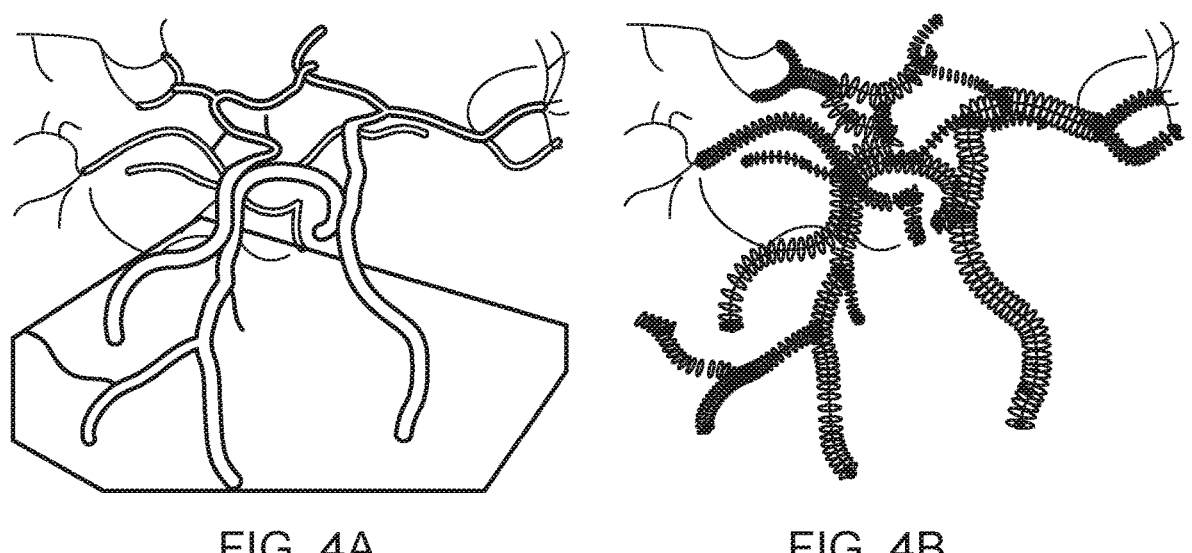
Figure 4C:
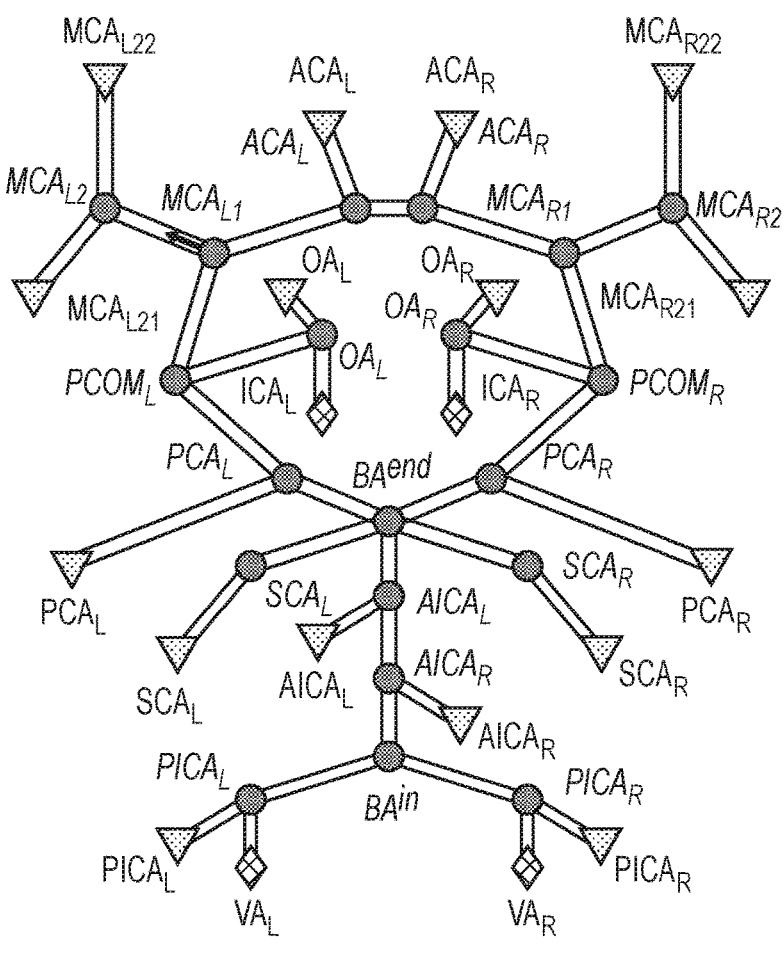

FIG. 4C illustrates a graph that can be determined based on the extracted configuration shown in FIG. 4B. The graph efficiently represents the layout of the vascular structure of the Circle of Willis as captured in the image shown in FIG. 4A, which each identified branch corresponding to an edge of the graph and each identified connection between branches corresponding to a vertex of the graph. Based on this graph, computational fluid dynamic techniques can be used to determine blood flow and blood pressure values for each edge and vertex by applying boundary conditions at the inlets and outlets of the network.

Figures 4D, 4E:
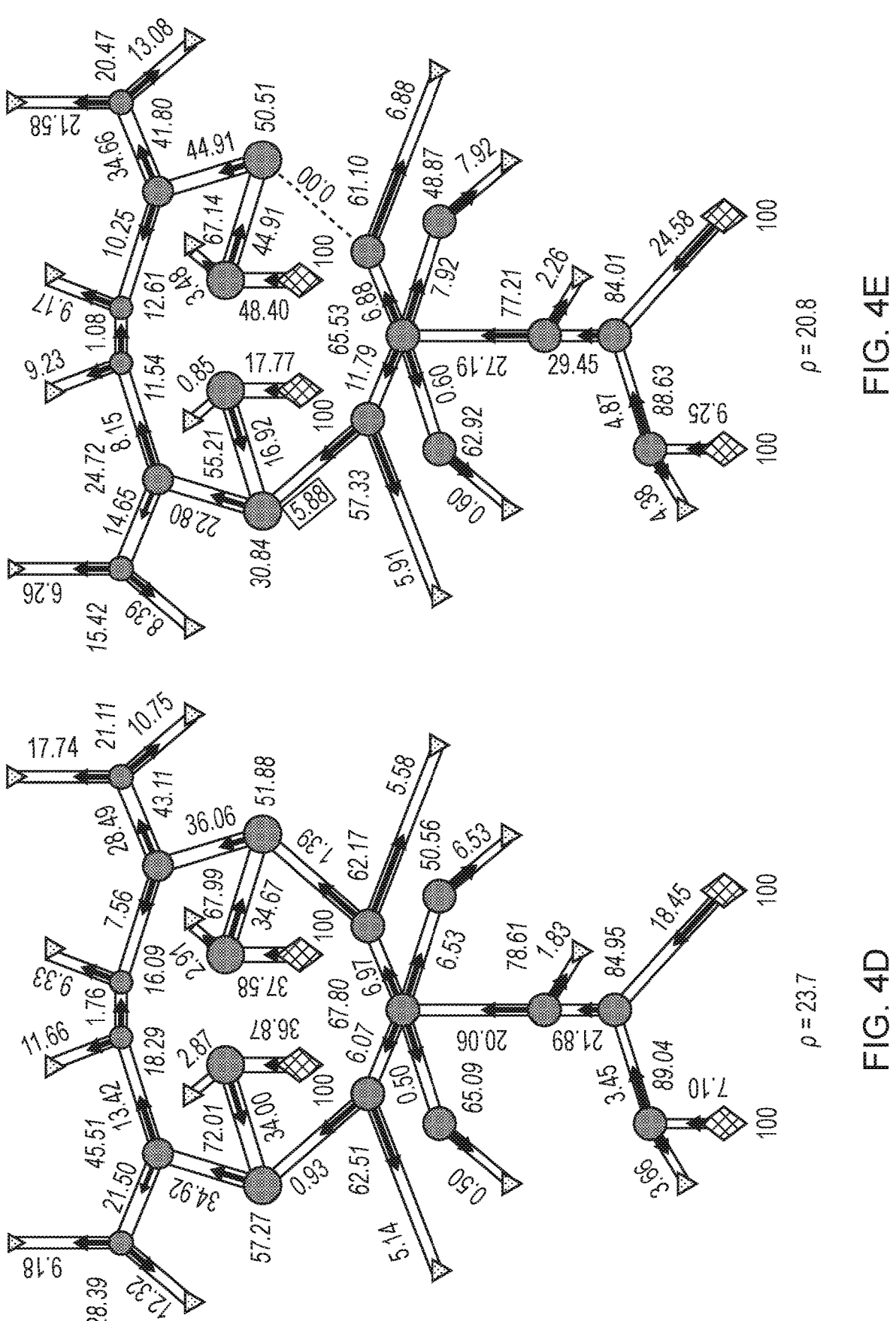

FIG. 4D illustrates the graph of FIG. 4C, with the aforementioned blood pressure and blood flow values shown. Based on this, a resilience value p of 23.7 has been determined to quantify the resilience of the imaged vascular structure to hypertension. An example of determination of such a resilience value is set out in more detail below.

FIG. 4E illustrates the graph of FIG. 4D, having been modified by the removal of the lower-right edge within the Circle of Willis structure (shown with a dotted line). The blood pressure and flow values have been recalculated for the modified structure, and a corresponding resilience value of 20.8 has been determined. It can thus be seen that the removal of this part of the Circle of Willis causes a notable reduction in the resilience to hypertension. The present technique can thus be used to example the impact on hypertension of modifications to the neurovascular structure, and thereby inform medical decision-making.

In general, modifications such as those described above can account for impedance modulations of the vessels, i.e. the local edge attributes, as well as for structural occlusions (or bypasses), i.e. connectivity patterns alterations, at different levels in the graph. Graph-based perturbations such as this can model key pathological scenarios, such as selectively altering the geometry of certain vessels, the presence of localised ischaemia or specific surgical repair. Alternatively, graph-based perturbations can model a number of randomly generated complications over the entire vascular network at different degrees, e.g. widespread increase of vascular stiffness, lumen stenosis and vessel tortuosity on a long-term scenario. The diffusion profiles of the vascular network and their distributions are assessed for specific graph configurations. Given the connected form of the vascular graph, functional mechanisms of network autoregulation and compensation can be globally and locally simulated for mild-to-moderate perturbations reproducing in-silico different levels of impairment. Statistical biomarkers of vascular resilience (or vulnerability) are determined from the graph diffusion and territorial supply, by analysing variations and deviations of hemodynamic quantities on randomised alterations. Risk stratification and advanced graph-based statistical analyses can be used for groups of vascular networks showing similar topologies, i.e. with similar anatomical phenotypes.

Figure 5:
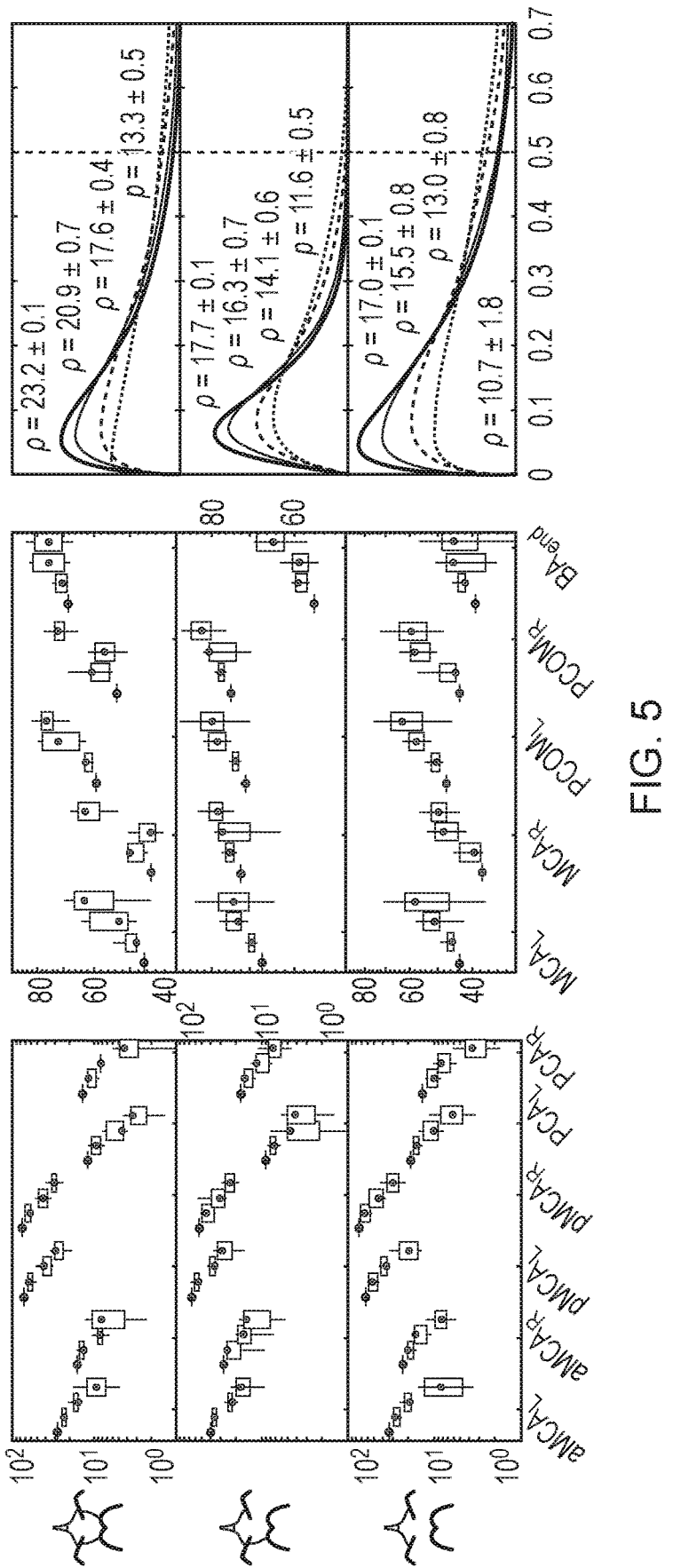
FIG. 5 shows the results of randomly perturbing graphs corresponding to three different anatomical phenotypes, each being a different Circle of Willis configuration.

FIG. 5 shows the results of randomly perturbing graphs corresponding to three different anatomical phenotypes, each being a different Circle of Willis configuration. On the left, a schematic representation of each Circle of Willis configuration is shown. Adjacent to this, graphs of flow (left) and pressure (centre) show the distributions of flow and pressure determined based on random perturbations of graphs corresponding to each configuration. Finally, on the right of the image a statistical distribution of the resilience to hypertension is shown for each configuration is shown. The present technique can thus be used to show that as elements of the Circle of Willis are removed, resilience to hypertension reduces.

A detailed example of extraction and modelling of a branched biological structure will now be described. The skilled person will appreciate that this is merely an example, and other techniques are possible.

Diffeomorphic Image Reformatting

Considering an angiographic image $V:\mathbb{R}^3 \to \mathbb{R}$ and given a geometrical centerline, or vascular minimal path, x from a topologically connected set $\Pi$, a reformatted volume $V_{rf}$ can be obtained by intersecting V with orthogonal cross-sections to $\pi$, these being further mapped with planar diffeomorphisms. The centreline $\pi = \{p_{i=1,l}\}$ in this example is a smoothly continuous sequence of length l, constituted of 3D points $p_i = \langle p_{i1}\underline{x}, p_{i2}\underline{y}, p_{i3}\underline{z} \rangle$ with $\{\underline{x}, \underline{y}, \underline{z}\}$ the canonical Cartesian image reference system.

The associated set of orthogonal planes $\pi^\perp = \{$ $$\pi^\perp = \{\underline{\pi}^\perp_{i=[0,l]}\}$$

is derived from the first-order gauge coordinates system, and the orthogonal plane $$\underline{\pi}^\perp_i$$

for the generic i-th point can be defined as a pair of orthonormal bases in 3D $$\underline{\pi}_i^{\perp} = \begin{bmatrix} \underline{e}_{1i} \\ \underline{e}_{2i} \end{bmatrix}, \text{ with} \begin{cases} \underline{e}_{1i} = \dfrac{\dfrac{\nabla \pi_i + \theta}{|\nabla \pi_i + \theta|} - \left(\left(\underline{\tau}_i \cdot \dfrac{\nabla \pi_i + \theta}{|\nabla \pi_i + \theta|}\right) \cdot \underline{\tau}_i\right)}{\left|\dfrac{\nabla \pi_i + \theta}{|\nabla \pi_i + \theta|} - \left(\left(\underline{\tau}_i \cdot \dfrac{\nabla \pi_i + \theta}{|\nabla \pi_i + \theta|}\right) \cdot \underline{\tau}_i\right)\right|} \\ \underline{e}_{2i} = \underline{\tau}_i \times \underline{e}_{1i} \end{cases}$$

where $$\underline{\tau}_i = \frac{\nabla \pi_i}{|\nabla \pi_i|} \text{ and } \nabla \pi_i = \left[\frac{\partial}{\partial \underline{x}} P_i, \frac{\partial}{\partial \underline{y}} P_i, \frac{\partial}{\partial \underline{z}} P_i\right], i = [0, l],$$

being $\nabla$ the spatial gradient operator, $\underline{\tau}_i$ the tangential unit vector of $\pi$ at $p_i$, and $\theta$ an arbitrarily small scalar value. The reformatted image $V_{rf}$ is recovered $$V_{rf} = V \cap \pi^{\perp} = \left\{V \big|_{\underline{\pi}_i^{\perp}}, i = [0, l]\right\},$$

where the angiography V is first evaluated on the set of orthogonal planes, these being then linearly transformed from the original system to the reformatted one with a diffeomorphism $\phi: \mathbb{R}^3 \to \mathbb{R}^3$, so that $\{\underline{\mathcal{X}}, \underline{y}, \underline{\mathcal{Z}}\} \xrightarrow{\mathcal{T}} \{\underline{x}' = \underline{e}_1,$ $\underline{y}' = \underline{e}_2, \underline{z}' = \underline{\mathcal{T}}\}$; being $\phi$ a 3D rotation group. In the formatted system, $\pi'$ is linearly and smoothly mapped along the $\underline{z}'$ axis of $V_{rf}$ for its entire length l, i.e.

$$\pi' = \{p'_{i=[0,l]}\}, \text{ with } p'_i = \langle 0\underline{x}', 0\underline{y}', i\underline{z}'\rangle.$$

Also, the reformatted image $V_{rf}: \mathbb{R}^3 \to \mathbb{R}$ is re-defined over a planar domain of arbitrary distal range 2Q.

Antagonist Diffusion

Two simultaneous and antagonist level-sets can be formulated over $V_{rf}$ to determine an implicit functional of vascular boundaries as energetic potential for the extraction of geodesic active contours. A diffusion equation describes the infinitesimal collective motion in a medium $$\frac{\partial \mathcal{U}(x', t)}{\partial t} = \nabla \cdot [D(\mathcal{U}, x') \nabla \mathcal{U}(x', t)],$$

With $\nabla u(x',t)$ being the spatial density of the diffusion medium at location $x' \in \{\underline{x}', \underline{y}', \underline{z}'\}$ at time t, and $D(u,x')$ being the associated tensor of diffusion coefficient at the same point. The motion of a front-wave propagation can be integrated and approximated using the anisotropic Eikonal equation. In the present example, two antagonist iso-levels of the diffusive arrival time $U_{int}$ and $U_{ext}$ are integrated for the discrete medium $V_{rf}$ under the following configurations:

$$u_{int}(x) = \min \int_{x'} \sqrt{(\nabla V_{rf}(x'))^T D(x')(\nabla V_{rf}(x'))} dx',$$

$$u_{ext}(x') = \min \int_{x'} \sqrt{(\nabla \overline{V}_{rf}(x'))^T D(x')(\nabla \overline{V}_{rf}(x'))} dx',$$

with $\overline{V}_{rf}$ the negative image of $V_{rf}$. Note that, adopting a constant tensor D=13, the anisotropic level-set boils down to an isotropic wave-front propagation that can be solved with a Fast Marching implementation, imposing $|\nabla u(x')|=1$ and u(s)=0, with s the initial set of seeds on a finite grid. The initialisation seeds $s_{int}$ are the points of the discretised reformatted centreline, i.e. $s_{int}=\pi'$, being these inside the vascular structure; whereas, we consider the furthermost longitudinal edges of the finite domain in $\nabla_{rf}$ as the initial set of seeds $s_{ext}=\{x'=\langle |Q|\underline{x}', |Q|\underline{y}', i\underline{z}'\rangle, \forall i=0, 1, \ldots [l]\}$. $U_{int}$ models the diffusive process within the blood vessel, which propagates first along the lumen towards the vessel wall, whereas $U_{ext}$ models the containing effect of external parenchymal structures surrounding the vascular network. In this example, both level-sets will propagate over $V_{rf}$ and $\overline{V}_{rf}$ respectively, eventually leaking into the mutual structures. Exploiting the monotonic profiles of $U_{int}$ and $U_{ext}$, and combining their antagonist diffusing behaviours, a vascular boundary energy potential P can be determined as $\mathcal{P} = (\mathcal{U}_{int} + \mathcal{U}_{ext}) + |\mathcal{U}_{int} - \mathcal{U}_{ext}|$. The boundary energy potential P implicitly encodes the geometrical locus of the competing frontier between the considered level-sets, with pronounced local minima (valleys) in the neighbourhood of the vessels' wall.

Geodesic Active Contours (G-Snakes)

Leveraging the geometry of $V_{rf}$, a constrained geodesic active contour (G-snake) is evolved on the vascular boundary energy potential P following an iterative normal motion direction $$\frac{\partial \sigma(x', t)}{\partial t} = -(\nabla \mathcal{P}(x') \cdot \underline{n}) \cdot \underline{n},$$

where, in this case, $\underline{n}$ is the radial unit vector joining $p'_i$ and any other point of $\sigma$. Note that $\sigma$ is initialised as a circular closed contour, and iteratively evolves with a gradient descent towards the valleys so that an integral energy F is jointly minimised along the snake, i.e., $\mathcal{F} = \min \int_{\sigma} \mathcal{P}(\sigma) d\sigma$, at convergence.

Hybrid 0-D Hemodynamic Analog-Equivalents

A vascular hybrid equivalent is automatically recovered from the geometrical model under a simplified hemodynamic setup. Connected biomechanical lumped parameters are translated into an analog closed-circuit configuration, simulating approximations of blood flow and pressure drop. Topological perturbations and network variants are lastly modelled for the underlying vascular graph.

Hemodynamic Lumped-Parameters Model

Hemodynamic quantities are obtained from simplifying the Navier-Stokes equations, governing the three dimensional theory of fluid dynamics in the continuum. For the vascular branch embedded in $V_{rf}$, we adopt a cylindrical approximation of the underlying geometry, where a rigid pipe runs with fixed radius along the axial direction $\underline{z}'$. The axial motion of a fluid is derived from the Cauchy momentum of mass conservation to the differential Hagen-Poiseuille equation $$q_{z'}^{max} = -\frac{1}{4\mu} \frac{\partial p}{\partial \underline{z}'} \cdot r^2,$$

under the assumption of a steady i.e.

$$\frac{\partial q}{\partial t} = 0,$$

fully-developed i.e.

$$\frac{\partial q_{z'}}{\partial z'} = 0,$$

and axisymmetric flow q, showing non-turbulent motion, i.e. with null flow velocity for both radial and swirl components. The maximum flow occurs at the center of the pipe of radius r, and the constant average axial flow $$\overline{q}_{z'} = \frac{1}{2} q_{z'}^{max}$$

integrates its parabolic profile over the pipe's cross-section. Integrating also a linearly decreasing pressure drop $\partial p$ along the entire length l of the pipe, a constant, average, axial blood flow $Q = \overline{q}_{z'}$ can be rewritten as $$Q = \frac{\Delta P}{R}, \text{ with } R = \frac{8\mu l}{\pi r^4},$$

$\Delta P$ being the integral pressure gradient, R the average resistance of the rigid pipe of radius r, and $\mu$ being the constant blood viscosity. Note that in the above equation, $\pi$ is the Archimedes' constant. Also, following the above linearisation, the constant radius r is the integral average $$r = \frac{1}{l} \int_{l_i} \sqrt{\frac{A(\sigma(z'))}{\pi}} \, dz',$$

with $A(\sigma(\underline{z}'))$ being the area of the cross-sectional G-snake recovered as described above along $\underline{z}'$.

0-D Topological Analog-Equivalent Along with the hydraulic analogy of electric systems, in the present example analog-equivalent circuits are modelled as a set of connected lumped parameters for the vascular network encoded in $\Pi$. A generic vascular topology $\Pi=(N,E)$ is defined as a set of nodes $j=1, \ldots, |N|$ (i.e. the branch-points), and the associated connecting edges $\pi(j_1,j_2)$ (i.e. the vascular branches), encode in $E(j_1,j_2)$ the binary adjacency matrix. For each connected $\pi(j_1,j_2)$, the tubular mechanical features are converted into electrical impedance, i.e. resistance, compliance and inertance, for a fully-dynamic equivalent. In the present example, given the steady flow, purely dynamic components vanish in the model, and the impedances of the connected pipes simplifies to real-valued scalar resistances R=f(l, r) as in the equation above. For compactness, these are embedded in the associated resistance-weighted adjacency matrix $$R(j_1, j_2) = R_{\pi(j_1, j_2)}.$$

In a similar matricial form, the blood flow $Q(j_1,j_2)$ and the pressure drop $\Delta P(j_1,j_2)$ are translated into current and potential difference for each vascular branch, respectively. Simulating a closed-loop analog circuit, voltage generators $(SRC_j)$ as well as potential grounds $(GND_j)$ are introduced in the system, these modelling the blood pressure at the inlets and outlets of the network as node-wise potential boundary conditions $(P_{BC})$. Given the linear lumped electrical elements and leveraging the connectivity of the vascular network, the analog-equivalent circuit is solved using Kirchhoff's laws, as a linear system of equations. As described in the following algorithm:

Input: R, $P_{BC}$
Output: P, $\Delta$P, Q $C_{R_d} = 0_{|N| \times |N|}$; $^C R_{\overline{d}} = 0_{|N| \times |N|}$; $C_{P_{BC}} = 0_{|N| \times 1}$:      ▷ Initialisation
for all $E(j_1, j_2)$=1 do $^C R_{\overline{d}} (j_1, j_2) = {}^C R_{\overline{d}}(j_1, j_2) - R(j_1, j_2)^{-1}$:
    $C_{R_d}(j_1, j_1) = C_{R_d} (j_1, j_1) + R(j_1, j_1)^{-1}$:
    $C_{R_d}(j_2, j_2) = C_{R_d}(j_2, j_2) + R(j_2, j_2)^{-1}$:

$C_R = (^C R_{\overline{d}} + {}^C R_{\overline{d}} ) + C_{R_d}$:      ▷ Circuit Admittance System
for all $P_{BC_j} \in \{SRC, GND\}$ do
    $C_R(j_{1=j}, \forall j_2) = 0$:
    $C_R(j_{1=j}, j_{2=j}) = 1$:
    $C_{P_{BC}}(j_{1=j}) = P_{BC_j}$:      ▷ Include Boundary Conditions
    $P = C_R^{-1} C_{PB}$:      ▷ Solve the Linear System
for all $E(j_1, j_2)$=1 do
    $\Delta P(j_1, j_2) = P(j_1) - P(j_2)$:      ▷ Assign Potential Difference
    $Q(j_1, j_2) = \Delta P(j_1, j_2) \cdot R(j_1, j_2)^{-1}$:      ▷ Assign Current (Ohm's law)

$C_{R_d}$ and $C_{R_{\overline{d}}}$ are the respective diagonal and off-diagonal components of the total circuit admittance system matrix $C_R$; $C_{PBC}$ is the node-wise potential vector of boundary conditions, and P is the resulting node-wise potential (i.e. branch-point blood pressure) from solving the linear system of equations.

Modelling Perturbations on Vascular Topologies Two alterations account for a structural connectivity perturbation of the original network, and a modulation M of the associated resistance-weighted adjacency matrix. The structurally perturbed topology is defined as $\tilde{E}=\varepsilon \circ (E \circ \mathcal{A})$ where $\varepsilon(j_1,j_2) \sim B(\lambda)$.

Binary values in $\varepsilon$ follow a Bernoulli distribution B of probability $\lambda$, these modelling random occlusions, which disrupt the connectivity by a factor $\varepsilon=(1-\lambda)$, on average. A is an anatomical prior; non-zero edges $A(j_1, j_2)$ weight the likelihood of certain cerebrovascular connections. In general A is unknown for $\Pi$, meaning that $\mathcal{A} = 1_{|N| \times |N|}$, therefore vanishing in the above equation; available knowledge of connected branch-points can be however embedded in A for labelled annotations. Given $\tilde{E}$, the associated resistance matrix $R_{\tilde{E}}(j_1, j_2)$ can be recovered as described in the previous section. Further vascular stenoses and increased vessel tortuosity are modelled for both reduced radii r and longer pipes' lengths l, respectively. These are compactly integrated in $\tilde{R}_E = \mathcal{M} \circ R_{\tilde{E}}$, with $\mathcal{M}(j_1, j_2) \sim 1 - U(0, m)$ following a uniform distribution with $m < 1$. Note that the impact of stenosis is predominant over tortuosity, since the equivalent $$R \propto \frac{1}{r^4}.$$

Hemodynamics on Anatomically Exact Topologies (CoW)

Blood pressure potentials are initialised at the anatomical inlets, whereas potential grounds are set at the terminal branches of the Circle of Willis (CoW—see FIGS. 4A to 4C and the description thereof). Given A for the considered topologies, we first evaluate autoregulation mechanisms by simulating a stenotic Internal Carotid Artery (ICA) and an occlusion of the Posterior Communicating Artery (PCOM), as to validate the software implementation of the model in a simple scenario. Simulations are then computed by perturbing only the resistance-equivalents, where fluctuations in M modulate both radius and length of the pipes. Perturbations account for 3 classes with maximal resistance increment $m^{max} = 50\%$, and a total $n = 1000$ instances per class. Hemodynamics are simulated on unperturbed and altered equivalents for comparison. The obtained quantities are then averaged across topological instances of the same type, for the n simulated perturbations. Lastly, a global network resilience Px metric can be estimated, defined for the simulated instance as $$\rho_\Pi = \frac{1}{|E|} \sum_{|\tilde{E}d|} \rho$$

with $$\rho = \frac{(\Delta P \cdot Q)}{\pi r^{2l}},$$

where $|\tilde{E}|$ is the total number of vascular branches after the topological perturbation (here $\varepsilon = 1_{|N| \times |N|}$), and $|\tilde{E}_d|$ represents the diffused ones, i.e. those having non-zero Q and $\Delta P$. The scalar index $\rho_\pi$ is an integral surrogate for the branch functionality after the perturbation over the network. Assuming healthy networks being well diffused, $\rho_\pi$ is maximal for unperturbed analog-equivalents, whereas it decreases along with impairing perturbations.

As illustrated in FIGS. 4C-4D, autoregulation mechanisms are simulated for different topologies of the Circle of Willis. On average, reduced blood flow and pressure values are observed for the perturbed ipsilateral branch of the vascular network, whereas overall minimally affected hemodynamic quantities are found for the remaining part of the perturbed topologies. While blood flow is marginal in the PCOMs for the unperturbed network (FIG. 4C), it remarkably increases after the simulated stenosis and occlusion (highlighted edges), where the flow overdraft is mainly compensated by the posterior circulation. Similar autoregulation mechanisms can be observed for other topologies, where major compensations are given by the anterior left-right circulatory contribution at the level of the Anterior Communicating Artery (ACA). This is mainly due to the intrinsically different redundancy of the CoW in these topologies. In these cases, despite the relatively small size of the ACA, increased blood flow is reported and highlighted for the part of the network contro-lateral to the simulated perturbation. Lastly, resilience indices p are reported for all the considered topologies, these showing a decreasing trend for the same perturbation on different networks. In FIG. 5 the blood flow and pressure distributions (boxplots) are reported for representative edges and nodes of the CoW. The hemodynamic quantities of the considered 3 classes of perturbations (i.e $0 < m_1 < 0.2$, $0.2 < m_2 < 0.3$, and $0.3 < m_3 < 0.5$) are compared against the unperturbed values. On average, blood flow shows a decreasing trend, in line with the overall increased impedance of the vascular network. Conversely, the distributed pressure on relevant branch-points of the CoW shows a progressive increase with the level of the perturbation, with relatively smaller increase ratio for the terminal point of the Basilar Artery ($BA^{end}$). Also, in FIG. 5 the hypertension histogram is fitted with a gamma distribution for all topologies and for all perturbation levels. Here, hypertension is defined as the pressure normalised by the cross-sectional area of the vessel.

Unperturbed CoW show a hypertension profile rather skewed towards low values. When increasing perturbations, the associated histogram shows a broader profile with an overall increasing number of small vessels reporting a relatively high pressure. This suggests that for increased stenoses a level of hypertension on the CoW tends to distribute over the whole vascular network, with more pronounced risk of ruptures and hemorrhagic events above a certain threshold (e.g. the dashed line in FIG. 5). Also note that due the simulated stenosis, there is also a higher prevalence of zero-force regions in the hypertension histogram, suggesting higher risk of ischemia. Lastly, decreasing resilience indices p are found for all topologies at increasing perturbations.

Hemodynamics on Redundant Uncertain Topologies (CoW)

So far, validations have assumed a specific realisation of an underlying vascular tree. However, robustly extracting vascular trees can present difficulties. In this section it is demonstrated that the simulation framework described herein can be used to test the plausibility of hypothetical trees, allowing the pruning of hemodynamically implausible trees.

Figure 6:
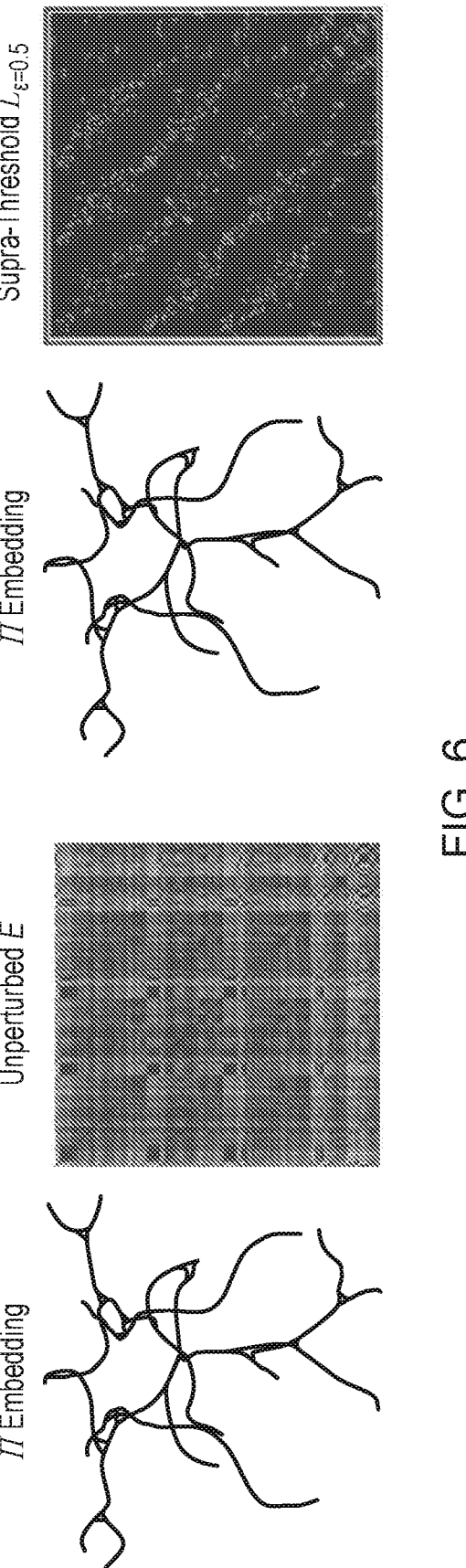
FIG. 6 shows a representative example for a fully-connected vascular graph.

Relaxing the assumption of a known A, topological perturbations & are introduced for a representative over-connected vascular graph IT, which embeds uncertain connections among vascular junctions. Similarly as described above, boundary conditions are initialised for those nodes closest to the annotated in/outlets; however, no modulation of the resistance-equivalent is performed here, i.e. $\mathcal{M} = 1_{|N| \times |N|}$. Modelling complete occlusions of the redundant network and simulating their hemodynamic behaviour stand as iteratively sampling vascular subnets and evaluating their physiological compatibility among the comprehensive pool embedded in Π. Randomly perturbed classes of topologies $\tilde{\Pi}$ are generated for $\varepsilon = 0.2; 0.3; 0.5$, each accounting a total $n = 1000$ instances. For each class of binary perturbation, an inverse resilience adjacency matrix $\hat{\rho}$ of the same size as $\tilde{E}$, is determined as $\hat{\rho}(j_1, j_2) = \rho(j_1 j_2)^{-1}$, and an associated hemodynamic likelihood matrix $\mathcal{L}$ is integrated for all simulations in each class $\mathcal{L} = \Sigma_n \rho_n \cdot MST(\hat{\rho}^n)$, where MST is the minimum spanning tree maximising the intrinsic resilience of each perturbed topology. In this manner, a subset of connected branches can be automatically reconstructed from the uncertain topology, these being most hemodynamically compatible, by maximising the associated resilience and by integrating multiple overlapping minimum spanning trees. In FIG. 6 a representative example is shown for an fully 17 18 connected vascular graph $\Pi$ and for the associated subset of most hemodynamically compatible branches $\hat{\Pi}$. In this case, $\varepsilon=0{:}5$ and the recovered likelihood $\mathcal{L}$ is thresholded for values above the median. The supra-threshold $\hat{\Pi}$ shows a dramatically reduced redundancy in the connectivity pattern (adjacency matrix), however the completeness of the CoW topology is kept overall intact. Similar results are observed for $\varepsilon=0.2$; 0.3, these showing however a decreased sparsity in the uncertain topology. This suggests that for $n\rightarrow\infty$ simulations and for topological perturbations of different degrees, a family of physiologically compatible graphs statistically emerges from the uncertain and redundant topology $\Pi$, by jointly maximising the subnet resilience and by integrating overlapping minimal acyclic realisations.

Discussion of the Above-Described Example

Above is described a hemodynamic 0-D topological framework for neurovascular simulations, which statistically estimates biomarkers from a series of topological perturbations of the original vascular network. By means of a biomechanical lumped-parameters model obtained from geodesic snakes on a reformatted vascular image, hemodynamic quantities are estimated for branches and branchpoints of vascular topologies. First, vessel walls segmentation with G-snakes provides similar accuracy to comparative vascular segmentation tool-kits. Even though mean radius errors are limited to the voxelsize, with maximal deviations of ~1 mm, such deviations are negligible for the presented hemodynamic simulations due to the subsequent constant-radius pipe assumption of the topological-hemodynamic model. The level of approximation adopted in the formulation cannot fully model vascular fluid-structure interactions (i.e. wall-tissue stress), nor the effect of a pulsating blood flow and pressure. However, the inexpensive computational cost ($0.4\pm0.2$ ms per simulation), the arbitrary scalability of the 0-D analog-equivalents and the flexibility for network perturbation, i.e. occlusions, stenoses and tortuosity, allow an early evaluation of the mechanisms underlying the cerebral blood autoregulation in a compact and reproducible way. Functional vascular parameters such as blood flow and pressure (drop) can be recovered for the vascular branches and branch-points by solving an associated impedance analog-equivalent with extra boundary conditions i.e. voltage sources and grounds. Also biomarkers and surrogate indices can be defined to automatically characterise the resilience of the vascular network to perturbations and alterations. For three different CoW topologies both local autoregulation mechanisms and functional features distributions can be evaluated with an arbitrarily defined perturbation first, then with a series of random morphological modulations spanning over all the vascular network. Results on exact topologies from the presently described data-driven neurovascular simulations are in line with comparative studies based on an artificial physiological model embedding similar lumped-parameters. Such models correlate well with fully-resolved fluid dynamic simulations and real measurements, as flow-rate inaccuracies from bifurcation angles can be compensated with extra impedances. Lastly, a hemodynamically compatible vascular graph sampling procedure can be formulated for uncertain redundant topologies, where a family of physiologically compatible graphs statistically emerge from jointly maximising the subnet resilience and integrating overlapping minimal spanning trees.

Through use of the above described techniques, it will be appreciated that biological characteristics corresponding to branched biological structures can be efficiently determined.

Methods described herein may be performed in hardware and/or software. Such hardware may be a general-purpose processor, or a more specific unit such as an application-specific integrated circuit or a field-programmable gate array.

Although illustrative examples of the invention have been described in detail herein with reference to the accompanying drawings, it is to be understood that the invention is not limited to those precise examples, and that various changes, additions and modifications can be effected therein by one skilled in the art without departing from the scope of the invention as defined by the appended claims. For example, various combinations of the features of the dependent claims could be made with the features of the independent claims without departing from the scope of the present invention.

The invention claimed is:

1. An apparatus comprising:

input circuitry configured to acquire imaging data corresponding to a branched biological structure; and image processing circuitry configured to:

extract, from the imaging data, a configuration of the branched biological structure;

determine graph data indicative of the configuration of the branched biological structure, wherein the graph data comprises edges corresponding to branches of the branched biological structure and vertices corresponding to connections between said branches of the branched biological structure, wherein the graph data is non-hierarchical graph data comprising one or more loops and multiple roots, and wherein the image processing circuitry is configured to, as part of the determining of the graph data:

determine for each said edge, at least one geometrical property of the corresponding branch of the branched biological structure; and determine a biomechanical lumped parameter associated to the geometrical property;

detect, based on the graph data, a biological characteristic of the branched biological structure, wherein the image processing circuitry is configured to, as part of the detecting a biological characteristic:

translate the determined biomechanical lumped parameters into an analog closed-circuit configuration; and simulate approximations of fluid flow and fluid pressure drop in said branched biological structure by solving said analog closed-circuit;

modify the graph data with a biologically plausible modification, wherein the image processing circuitry is configured to modify the graph data to at least one of remove at least one edge of the graph data and remove at least one node of the graph data;

re-detect, based on the modified graph data, the biological characteristic of the branched biological structure;

iteratively repeat the modifying of the graph data and the re-detecting of the biological characteristic;

based on the detection of the biological characteristic and the re-detections of the biological characteristic, determine a statistical likelihood associated with the biological characteristic; and based on the statistical likelihood, determine a statistical susceptibility of the branched biological structure to a pathology.

2. An apparatus according to claim 1, wherein said at least one geometrical property of the corresponding branch comprises at least one of:

a length of the corresponding branch; and a width of the corresponding branch.

3. An apparatus according to claim 1, wherein the image processing circuitry is configured to determine, for each said vertex and based on said geometric properties associated with each said edge, at least one fluid property associated with the corresponding connection of the branched biological structure, said detecting of the biological characteristic being based on said at least one fluid property of said vertices.

4. An apparatus according of claim 3, wherein said at least one fluid property associated with the corresponding connection comprises at least one of:

a fluid pressure at the corresponding connection; and a fluid flow through the corresponding connection.

5. An apparatus according to claim 3, wherein the image processing circuitry is configured to determine at least one fluid property associated with the corresponding connection of the branched biological structure by performing computational fluid dynamical modelling with the graph data as an input.

6. An apparatus according to claim 1, wherein the modifying of the graph data, by the image processing circuitry, corresponds to a modification of the configuration of the biological structure.

7. An apparatus according to claim 6, wherein the image processing circuitry is configured to determine the modification of the biological structure based on a potential future physical modification of the biological structure.

8. An apparatus according to claim 6, wherein the image processing circuitry is configured to modify the graph data to at least one of:

add at least one edge to the graph data;

add at least one node to the graph data;

modify a width associated with at least one edge of the graph data; and modify a length associated with at least one edge of the graph data.

9. An apparatus according to claim 1, wherein said branched biological structure is a network of blood vessels.

10. An apparatus according to claim 1, wherein the imaging data is an angiographic image and the image processing circuitry is configured to, as part of the determining of the graph data:

extracting a geometrical centerline, or vascular minimal path, $\pi$ from a topologically connected set II of the angiographic image; and obtaining a reformatted volume $V_{rf}$ by intersecting the angiographic image with orthogonal cross-sections to the geometrical centerline, or vascular minimal path, x, the orthogonal cross-sections being further mapped with planar diffeomorphisms.

11. An apparatus according to claim 1, wherein the image processing circuitry is configured to, as part of extracting the configuration of the branched biological structure:

delineating and segmenting the acquired imaging data by way of geodesic active contours.

12. A method comprising:

acquiring imaging data corresponding to a branched biological structure;

extracting, from the imaging data, a configuration of the branched biological structure;

determining graph data indicative of the configuration of the biological structure, wherein the graph data comprises edges corresponding to branches of the branched biological structure and vertices corresponding to connections between said branches of the branched biological structure, wherein the graph data is non-hierarchical graph data comprising one or more loops and multiple roots, and wherein determining the graph data comprises:

determining for each said edge, at least one geometrical property of the corresponding branch of the branched biological structure; and determining a biomechanical lumped parameter associated to the geometrical property;

detecting, based on the graph data, a biological characteristic of the branched biological structure, wherein detecting the biological characteristic comprises:

translating the determined biomechanical lumped parameters into an analog closed-circuit configuration; and simulating approximations of fluid flow and fluid pressure drop in said branched biological structure by solving said analog closed-circuit;

modifying the graph data with a biologically plausible modification, wherein modifying the graph data comprises at least one of removing at least one edge of the graph data and removing at least one node of the graph data;

re-detecting, based on the modified graph data, the biological characteristic of the branched biological structure;

iteratively repeating the modifying of the graph data and the re-detecting of the biological characteristic;

based on the detection of the biological characteristic and the re-detections of the biological characteristic, determining a statistical likelihood associated with the biological characteristic; and based on the statistical likelihood, determining a statistical susceptibility of the branched biological structure to a pathology.

13. A non-transitory computer-readable medium comprising computer-implementable instructions for causing a computer to become configured to carry out the method of claim 12.

* * * * *